United States Patent
Rang et al.

[11] Patent Number: 5,739,402
[45] Date of Patent: Apr. 14, 1998

[54] PROCESS FOR THE PREPARATION OF MIXTURES OF ISOMERS OF O-PHENOXY-ALKYLHYDROXYLAMINES OR O-PHENOXYALKYLOXIMES

[75] Inventors: Harald Rang, Altrip; Norbert Götz, Worms; Albrecht Harreus, Ludwigshafen; Dirk Borchers, Birkenheide; Horst Hartmann, Böhl-Iggelheim; Volker Maywald; Frank Heimann, both of Ludwigshafen; Thomas Buschulte, Böhl-Iggelheim, all of Germany

[73] Assignee: BASF Aktiengesellschaft, Ludwigshafen, Germany

[21] Appl. No.: 732,452
[22] PCT Filed: Apr. 26, 1995
[86] PCT No.: PCT/EP95/01581
§ 371 Date: Nov. 4, 1996
§ 102(e) Date: Nov. 4, 1996
[87] PCT Pub. No.: WO95/30648
PCT Pub. Date: Nov. 16, 1995

[30] Foreign Application Priority Data
May 5, 1994 [DE] Germany ............ 44 15 887.4

[51] Int. Cl.$^6$ .................................. C07C 209/52
[52] U.S. Cl. ............ 564/415; 564/256; 564/300; 564/413
[58] Field of Search ............ 564/256, 300, 564/415, 413

[56] References Cited

U.S. PATENT DOCUMENTS 4,514,406 4/1985 Ohsumi et al. ............ 514/352
4,647,698 3/1987 Henrick .................. 564/256

(List continued on next page.)

FOREIGN PATENT DOCUMENTS 2151817 12/1993 Canada.
023560 2/1981 European Pat. Off..

(List continued on next page.)

OTHER PUBLICATIONS

Andree et al., Houben–Weyl, Methoden der Organischen Chemie, Georg Thieme Verlag Stuttgart 1990, vol. E16a/1, pp. 214–250.

(List continued on next page.)

*Primary Examiner*—Brian M. Burn
*Attorney, Agent, or Firm*—Keil & Weinkauf

[57] ABSTRACT

Preparation of mixtures of O-phenoxyalkylhydroxylamines Ia and Ib (Ia):
$H_2N-O-CH_2-CH(R^1)-O-Ar$ (Ib):
$H_2N-O-CH(R^1)-CH_2-O-Ar$ and the corresponding salt mixtures by
a) converting mixtures of isomers of O-(2-hydroxyethyl) oximes IIa and IIb (IIa):

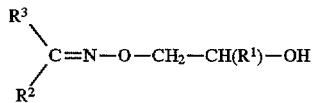

(IIb):

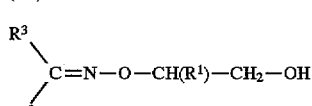

with a sulfonyl halide III (III):
Hal—SO$_2$—R$^4$   R$^4$ = organic radical
Hal = halogen into a mixture of sulfonates IVa and IVb (IVa):

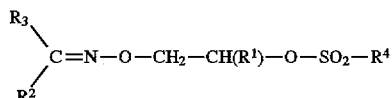

(IVb):

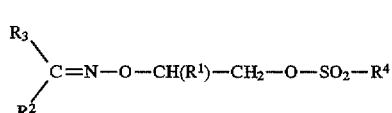

b) reacting this mixture of IVa and IVb with a phenol HO-Ar (V) to give a mixture of O-phenoxyalkoximes VIa and VIb (VIa):

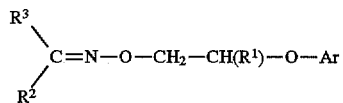

(VIb):

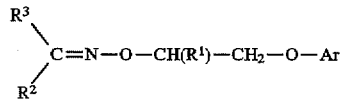

c) hydrolyzing this mixture in the presence of an acid and, if desired
d) liberating the O-phenoxyalkylhydroxylamines Ia and Ib from the resulting salts using a mineral acid.
Compounds Ia/Ib and VIa/VIb are important intermediates for crop protection agents.

19 Claims, No Drawings

U.S. PATENT DOCUMENTS

| | | | |
|---|---|---|---|
| 4,812,164 | 3/1989 | Wenger et al. | 71/92 |
| 4,859,229 | 8/1989 | Wenger et al. | 71/92 |
| 4,981,996 | 1/1991 | Wyss et al. | 564/300 |
| 5,120,849 | 6/1992 | Wild et al. | 546/334 |
| 5,382,685 | 1/1995 | Klein et al. | 564/301 |
| 5,393,921 | 2/1995 | Lazar et al. | 562/512 |
| 5,486,609 | 1/1996 | Reinhardt et al. | 544/173 |
| 5,585,520 | 12/1996 | Klein et al. | 564/300 |

FOREIGN PATENT DOCUMENTS

| | | |
|---|---|---|
| 4204206 | 2/1992 | Germany . |
| 258757 | 3/1990 | Japan . |
| 93/16033 | 8/1993 | WIPO . |

OTHER PUBLICATIONS

Klemm et al., Tetrahedron 20, 1676, 1671 (1964).

Markova et al., J. Org. Chem. USSR, 3, 1170 (1967).

Khomutov et al., Bioorganicheskaya Khimiya 12(12), 1662–1674 (1986).

Truitt et al., J. Am. Chem. Soc. 74, 3956/3957 (1952).

Niwa et al., J. Agric. Food Chem. 38, 514–520 (1990).

PROCESS FOR THE PREPARATION OF MIXTURES OF ISOMERS OF O-PHENOXY-ALKYLHYDROXYLAMINES OR O-PHENOXYALKYLOXIMES

The present application is a National Stage Application under 35 U.S.C. §371 of International Application No. PCT/EP 95/01581 filed Apr. 26, 1995.

DESCRIPTION

The present invention relates to a process for preparing mixtures of isomers of O-phenoxyalkylhydroxylamines of the formulae Ia and Ib

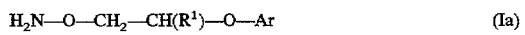
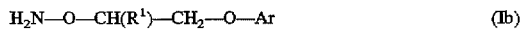

where $R^1$ is an alkyl group and Ar is the phenyl group which can carry nonaromatic substituents, and the corresponding salt mixtures.

The invention additionally relates to the preparation of mixtures of O-phenoxyalkyloximes of the formulae VIa and VIb

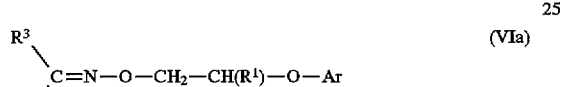

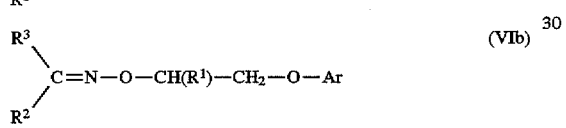

where $R^2$ is an alkyl group and $R^3$ is an alkyl or alkoxy group, or $R^2$ and $R^3$ form, together with the common carbon atom, a 5- to 7-membered isocyclic ring.

Furthermore, certain novel mixtures of isomers have been found.

The earlier German Application DE-A 42 44 390 discloses the reaction of oximes with phenoxyalkylating agents in the presence of a base to give O-phenoxyalkyloximes.

Furthermore, GB-A-2 115 812 discloses a process for preparing O-phenoxyalkyloximes in which the mesylate or tosylate of an O-alkylated oxime is reacted with a phenol, using a base.

Since the direct alkylation of hydroxylamine does not as a rule take place selectively on the oxygen atom, the processes for preparing O-phenoxyalkylhydroxylamines mostly make use of protective group techniques (cf. Houben-Weyl, Methoden der Organischen Chemie, Thieme Verlag, Stuttgart, 1990, Volume E16a/1, page 214 to page 250). In this connection, the use of N-hydroxyphthalimide as N-protected hydroxylamine has achieved particular importance. The required O-phenoxyalkylhydroxylamines are obtained starting from the latter by alkylation of the hydroxyl group and subsequent elimination of the phthalic acid moiety. This synthetic route has not, however, proven satisfactory because of the low yields and the loss of the protective group compound.

Hence, it was an object of the present invention to provide a more economic process for preparing O-phenoxyalkylhydroxylamines and O-phenoxyalkyloximes.

Accordingly, this object was achieved by a process for preparing mixtures of O-phenoxyalkylhydroxylamines of the formula I, which comprises a) converting a mixture of isomers of O-(2-hydroxyethyl) oximes of the formulae IIa and IIb

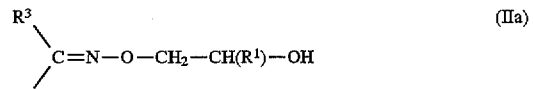

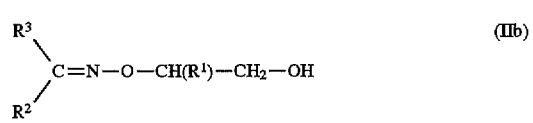

where $R^2$ is an alkyl group and $R^3$ is an alkyl or alkoxy group, or $R^2$ and $R^3$ form, together with the common carbon atom, a 5- to 7-membered isocyclic ring, with a sulfonyl halide of the formula III

where $R^4$ is an organic radical, and Hal is halogen, in the presence of a base into the corresponding mixture of sulfonates IVa and IVb

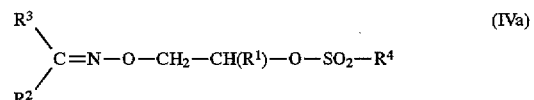

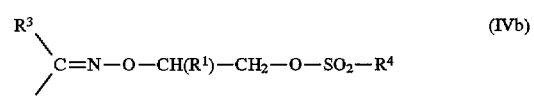

b) reacting this mixture of sulfonates in the presence of a base with a phenol of the formula V

to give a mixture of O-phenoxyalkyloximes of the formulae VIa and VIb

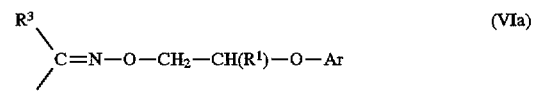

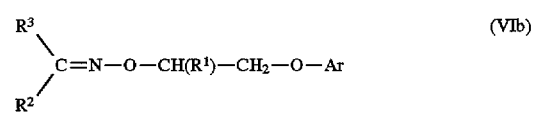

c) hydrolyzing this mixture in the presence of an acid and, optionally, d) liberating the O-phenoxyalkylhydroxylamines Ia and Ib from the resulting salts using a mineral base.

Furthermore, a process for preparing mixtures of O-phenoxyalkyloximes of the general formulae VIa and VIb was found which comprises the abovementioned process steps a) and b).

The invention also extends to mixtures of isomers of

O-[2-(4-chlorophenoxy)propyl] hydroxylammoniumbisulfate and O-[2-(4-chlorophenoxy)-1-methylethyl]hydroxylammonium bisulfate, O-[2-(4-chlorophenoxy)propyl] hydroxylammoniumchloride and O-[2-(4-chlorophenoxy)-1-methylethyl]hydroxylammonium chloride, 2-propanone O-[2-methylsulfonyloxypropyl]oxime and 2-propanone O-[2-methylsulfonyloxy-1-methylethyl]oxime.

The process according to the invention can be illustrated in a simple case as follows:

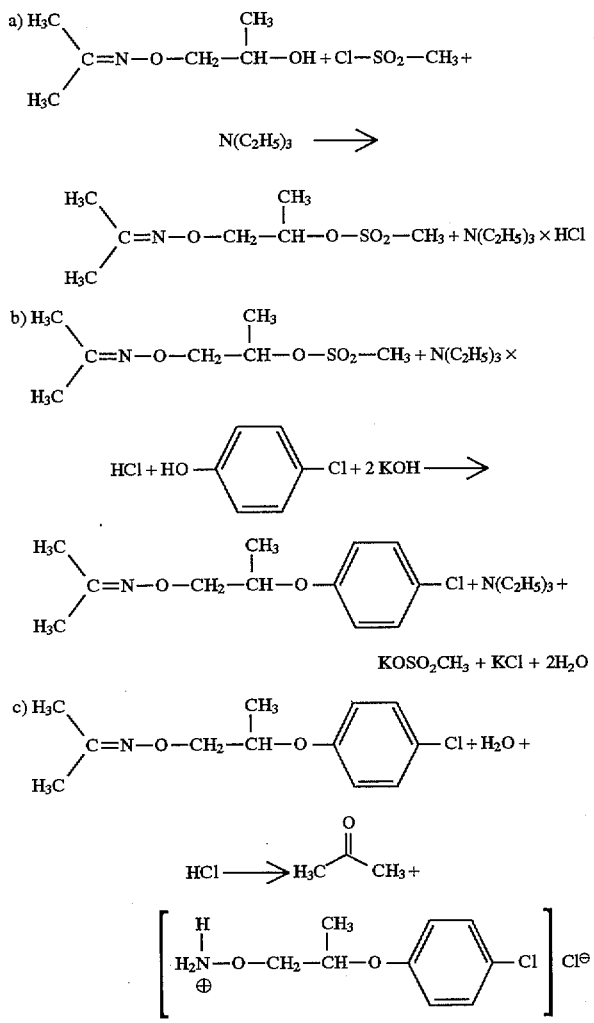

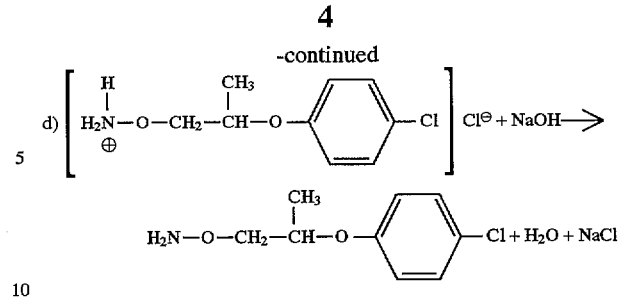

With a view to the active substances which can be prepared from the products VI and I, the individual variables preferably have the following meanings, both alone and in combination:

Ar is the phenyl group which can be unsubstituted or carry from one to three substituents, each selected from the group consisting of nitro, cyano, halogen, $C_1$-$C_4$-alkyl or $C_1$-$C_4$-haloalkyl, particularly preferably 4-halophenyl, especially 4-chlorophenyl;

$R^1$ is a $C_1$-$C_4$-alkyl group, particularly preferably methyl;

$R^2$ is a $C_1$-$C_4$-alkyl group and $R^3$ is a $C_1$-$C_4$-alkyl or $C_1$-$C_6$-alkoxy group or $R^2$ and $R^3$ form, together with the common carbon atom, a 5- to 7-membered isocyclic ring.

Particularly preferred O-phenoxyalkyloximes VI are those where $R^1$ and $R^2$ are an $C_1$-$C_4$-alkyl group, in particular the methyl and/or ethyl group, as well as the n-propyl and the n-butyl group.

Very particularly preferred O-phenoxyalkyloximes VI are those derived from acetone O-phenoxyalkyloxime, in particular 2-propanone O-[2-(4-chlorophenoxy)propyl]oxime.

Particularly preferred O-phenoxyalkylhydroxylamines I are those derived from the preferred and particularly preferred O-phenoxyalkyloximes VI as mentioned above.

The sulfonates IV can be obtained by reacting O-(2-hydroxyalkyl)oximes II with sulfonyl halides III in the presence of bases.

The O-(2-hydroxyalkyl)oximes II are known or can be prepared by known methods, for example by reacting the corresponding ketoximes VII with alkylene oxides VIII (cf., for example, U.S. Pat. No. 3,040,097; J. Am. Chem. Soc. 81, (1959) 4223 et. seq.) or the corresponding carbonates IX. As a rule, isomer mixtures of IIa and IIb are obtained.

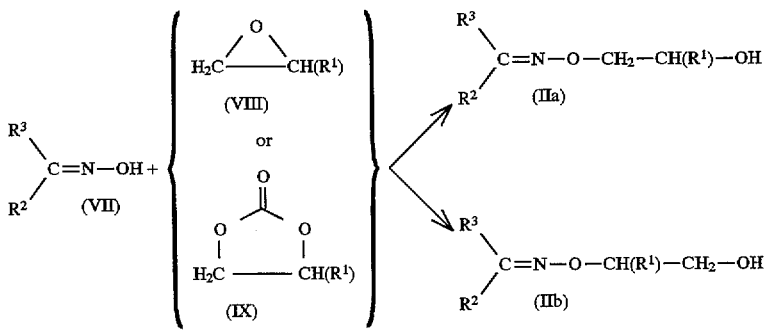

Suitable and preferred sulfonyl halides III are those where $R^4$ is a $C_1$-$C_4$-alkyl, $C_1$-$C_4$-haloalkyl or $C_1$-$C_4$-alkylphenyl group, and Hal is preferably chlorine and additionally bromine, especially methylsulfonyl chloride, trifluoromethylsulfonyl chloride and 4-methylphenyl sulfonyl chloride.

The sulfonyl halides III are commercially available or can be prepared by known methods, eg. by reacting the corresponding organic sulfonic acids with inorganic halogenating agents such as phosphorus pentachloride.

The molar ratio of O-(2-hydroxyalkyl)oxime II (ie. the total of IIa+IIb) to sulfonyl halide III is preferably from 1:1 to 1:1.5, in particular 1:1 to 1:1.2.

The reaction can be carried out without solvent or, especially, in an organic solvent.

Examples of suitable organic solvents are aliphatic hydrocarbons such as n-alkanes with more than 4 carbon atoms, especially n-pentane, and n-hexane, cycloalkanes such as cyclohexane, aromatic hydrocarbons, especially toluene and the xylenes, dipolar aprotic solvents such as ethers, especially diethyl ether, tetrahydrofuran and 1,4-dioxane, sulfoxides such as dimethyl sulfoxide and diethyl sulfoxide, sulfones such as dimethyl sulfone, diethyl sulfone and tetramethylene sulfone, nitriles such as acetonitrile and benzonitrile, N,N-disubstituted carboxamides such as dimethylformamide, N,N-dimethylbenzamide and N,N-dimethylacetamide, N-alkyllactams such as N-methylpyrrolidone and N-butylpyrrolidone, tetrasubstituted cyclic and acyclic ureas such as N,N,N',N'-tetramethyl- and -n-butylurea, and mixtures of the said solvents.

The reaction can, however, also be carried out in an excess of a suitable amine base as solvent.

The solvent or solvent mixture is generally employed in an amount of from 0.1 to 2, preferably 0.3 to 1, kg per mole of the O-(2-hydroxyalkyl)oxime II.

Suitable bases are inorganic and, preferably, organic bases, especially aliphatic tertiary amines such as triethylamine, tri-n-butylamine and N,N-dimethylcyclohexylamine and additionally aromatic tertiary amines such as pyridine and pyrimidine.

It is expedient to use per mole of the O-(2-hydroxyalkyl) oxime II from 1 to 2, in particular 1 to 1.5, equivalents of the base. If the base is also used as solvent, it is normally present in even larger excess.

The process is expediently carried out in such a way that the sulfonyl halide III is added to the mixture of isomers IIa and IIb and the base, with or without the solvent, and the mixture is heated to the reaction temperature.

As a rule, the reaction takes place at from -20 to 100, preferably 0° to 40° C., under pressures of from 0.5 to 2 bar. It is preferably carried out under atmospheric pressure. The starting materials have normally reacted completely after from 0.5 to 3 hours.

For working up, expediently water is added to the reaction mixture, and an organic phase which consists of or comprises the sulfonates IVa and IVb is isolated, usually with the assistance of an organic solvent such as toluene or diethyl ether.

The solvent is preferably removed by distillation, and this can be followed by further conventional purification operations such as distillation or recrystallization, resulting in the sulfonates IV (as purified mixture of IVa and IVb or the separated isomers) in pure form.

In a preferred embodiment of the process according to the invention, the organic phase after the extraction is transferred as such into the next stage where the mixture of sulfonates IVa and IVb is reacted with a phenol V in the presence of a base to give a mixture of O-phenoxyalkyloximes VIa and VIb.

In a particularly preferred embodiment of the process according to the invention, the crude reaction mixture is employed as such in the next stage.

The phenols V are commercially obtainable or can be prepared by known methods or ones similar thereto.

It is expedient to use per mole of the sulfonate IV (ie. the total of IVa and IVb) from 1 to 1.5 mol and, in particular equimolar amounts of the phenol V.

Mineral bases are preferably used as base, especially alkaline earth metal hydroxides or alkali metal hydroxides, in particular potassium hydroxide, and additionally sodium hydroxide or calcium hydroxide. Also suitable are sodium carbonate, potassium carbonate, sodium bicarbonate and potassium bicarbonate.

As a rule, from 1 to 5, preferably 1.5 to 3, mol of the base are used per mole of sulfonate IV (IVa+IVb).

The reaction can be carried out without solvent or in an organic solvent or solvent mixture.

Suitable organic solvents are especially methanol, ethanol and isopropanol or one of the solvents mentioned for process stage (a).

In general, the solvent or solvent mixture is employed in an amount of up to 2, preferably up to 1, kg per mole of the sulfonate IV.

As a rule, the reaction takes place at temperatures of from 20° to 180° C., preferably 40° to 100° C. The reaction usually takes from about 1 to 20 hours.

In the workup of the reaction mixture to the O-phenoxyalkyloxime I, as a rule first the volatile constituents, in particular water and, where appropriate, the solvent, are removed by distillation, and the crude O-phenoxyalkyloxime I is further purified if desired by conventional purification operations such as recrystallization, digestion or extraction using an organic solvent.

The yields of O-phenoxyalkyloximes VI (VIa and VIb together) are mostly between 60 and 90%.

If the mixture of O-phenoxyalkyloximes VIa and VIb subjected to acidic hydrolysis immediately after preparation thereof to give the salts of Ia and Ib, as a rule purification can be omitted.

Suitable acids for the hydrolysis are preferably protonic acids, especially sulfuric acid and hydrochloric acid, as well as phosphoric acid, trifluoroacetic acid and methanesulfonic acid, in particular in the form of their aqueous solutions.

The acids are, as a rule, used in the molar ratio of from 1:1 to 10:1, expediently from 5:1 to 7:1, based on the O-phenoxyalkyloxime VI (ie. the total of VIa and VIb).

The acidic cleavage of the mixture of VIb and VIb is expediently carried out in an inert solvent, especially water.

The reaction usually takes place at temperatures of from 50 to 130, preferably 60° to 80° C. and pressures of from 0.1 to 1, preferably from 0.3 to 0.5, bar. It can be carried out batchwise or continuously. The reactions as a rule take from 4 to 24, in particular 6 to 12, hours.

At the end of the reaction as a rule initially the liberated ketone ($R^2$—CO—$R^3$) and, where appropriate, the solvent are removed from the crude reaction mixture, especially by distillation.

A preferred embodiment of the process according to the invention, which is also particularly advantageous on its own, starts from a mixture of VIa and VIb, where $R^2$ and $R^3$ are methyl, and hydrolyzes the latter in the presence of sulfuric acid or hydrochloric acid. The acetone resulting from this is expediently removed continuously from the reaction mixture, during which part of the water and, when hydrochloric acid is used, also hydrogen chloride may also be carried over.

The crude reaction mixture is then worked up in a conventional way to give the salts of O-phenoxyalkylhydroxylamines Ia and Ib.

When hydrochloric acid is used, the workup is expediently carried out in such a that the hydrogen chloride and water which are still in the reaction vessel at the end of the reaction are removed as far as possible together azeotropic distillation.

The recovered excess acid can, in particular in the case of sulfuric acid and hydrochloric acid, be returned to the cleavage of the O-phenoxyalkyloximes VIa/VIb.

The remaining acidic salts of O-phenoxyalkylhydroxylamines Ia and Ib are then normally taken up in water.

The salts Is and Ib can, if desired, be obtained as such from the aqueous salt solution in a conventional way, eg. by concentrating the solution and crystallizing out.

When from 30 to 60% by weight sulfuric acid is used in the hydrolysis, as a rule crystallization of the bisulfates of Ia and Ib occurs just by cooling the reaction mixture to around 20° C.

The salt of the O-phenoxyalkylhydroxylamine Ia/Ib which has been precipitated in this way is separated from the supernatant solution in a conventional way, in particular by filtering off and washing the crystals, eg, with water and toluene.

Ia and Ib, together or after separation thereof, are liberated from their salts using a mineral base.

Suitable mineral bases are in particular alkali metal and alkaline earth metal hydroxides, carbonates and bicarbonates, with the hydroxides being preferred, and sodium, potassium or calcium hydroxide being particularly preferred.

It is expedient to use per mole of O-phenoxyalkylhydroxylamines I (ie. the total of Ia and Ib) from 1 to 3, in particular 1.1 to 1.5, equivalents of mineral base.

The neutralization is carried out in a conventional way so that details of this are unnecessary. This normally results in an organic phase which contains or consists of the O-phenoxyalkylhydroxylamines Ia and Ib, and a salt-containing aqueous phase.

The workup to the individual O-phenoxyalkylhydroxylamines Ia or Ib takes place by conventional techniques, especially by phase separation, extraction of the aqueous phase with an organic solvent such as toluene or diethyl ether, combination of the organic phases and subsequent removal of the solvent, especially by distillation. This can be, if desired, followed by further conventional purification operations such as distillation or recrystallization.

The yields of O-phenoxyalkylhydroxylamines I (Ia and Ib together) are usually about 80–90%.

The particular advantage of the process according to the invention is that a reduction in the content of the b isomer, which is often undesired with a view to the active substances which can be prepared from I, takes place in stages a), b) and c). Thus, it has been found that starting from mixtures of IIa and IIb in which the content of the isomer IIa is between 70 and 100%, particularly 70 to 99.5, and especially 70 to 98%, the resulting mixtures of isomers Ia and Ib contain a b isomer content which is from 75 to 98% lower.

It has furthermore been found that this reduction in the content of the b isomer as a rule takes place partly in stages a) and b), ie. during the preparation of the mixtures of VIa and VIb, and can often be improved further by carrying out the acidic hydrolysis thereof using sulfuric acid and then, or following the hydrolysis if another mineral acid is used, precipitating the O-phenoxyalkylhydroxylamines Ia and Ib as sulfates from the solutions obtained in this way.

The present process makes separation of the isomers IIa and IIb unnecessary. Since the mixtures resulting from the process are enriched in VIa or Ia, the preferred target products, purification thereof is much less elaborate even when it cannot be dispensed with entirely.

The products I and VI are suitable as precursors for herbicides of the cyclohexenone type (cf. e.g. EP-A 456 112).

PREPARATION EXAMPLES

Example 1

Preparation of 2-propanone O-[2-(4-chlorophenoxy) propyl]oxime and O-[2-(4-chlorophenoxy)propyl] hydroxylamine (Ia, VIa; $R^1$, $R^2$, $R^3$=methyl; Ar=4-chlorophenyl)

Variant 1 a) Preparation of the O-sulfonyloxyalkyloximes (IV)

57.3 kg (437 mol) of a mixture of 91.2% by weight 2-propanone O-(2-hydroxypropyl)oxime and 8.7% by weight 2-propanone O-(1-hydroxy-1-methylethyl)oxime were introduced into 66.3 kg (656 mol) of triethylamine and 175 kg of toluene. To the mixture were added, at 10°–20° C., 55.1 kg (481 mol) of methylsulfonyl chloride, and the mixture was then stirred at 25° C. for 1 hour. A sample of the crude product was worked up to the two main products:

2-propanone O-[2-methylsulfonyloxypropyl]oxime ($n_p^{22}$=1.4538):

$^1$H-NMR (400.1 MHz; in $d^6$-dimethyl sulfoxide): δ [ppm] =4.88 (1H, m); 4.05 (2H, d); 3.1 (3H, s); 1.83 (3H, s); 1.82 (3H, s); 1.3 (3H, d).

$^{13}$C-NMR (100.6 MHz; in $d^6$-dimethyl sulfoxide): δ [ppm]=155.4 (tert. C); 77.6 (CH); 74.7 (CH$_2$); 37.8 (CH$_3$); 21.2 (CH$_2$); 17.4 (CH$_3$); 15.4 (CH$_3$).

2-Propanone O-[2-methylsulfonyloxy-1-methylethyl] oxime ($n_p^{22}$=1.4520):

$^1$H-NMR (270.1 MHz; in $d^6$-dimethylsulfoxide): δ [ppm] =4.3 (1H, m); 4.25 (2H, m); 3.15 (3H, s); 1.82 (3H, s); 1.77 (3H, s); 1.2 (3H, d).

$^{13}$C-NMR (125.7 MHz; in $d^6$-dimethylsulfoxide): δ [ppm] =154.9 (tert. C); 75.0 (CH); 71.3 (CH$_2$); 36.6 (CH$_3$); 21.3 (CH$_3$); 15.7 (CH$_3$); 15.3 (CH$_3$).

b) Preparation of the O-phenoxyalkyloximes (VI)

Subsequently, while stirring, a solution of 56.4 kg (439 mol) of 4-chlorophenol in 147 kg of 40% strength (1.050 mol) potassium hydroxide solution was added. Toluene and triethylamine were then removed by distillation at 60° C. under 0.2 bar, and the reaction mixture was then stirred at this temperature for 16 hours.

After the crude product had been mixed with 150 l of water, the aqueous and organic phases were separated, and the aqueous phase was extracted with a total of 150 l of toluene. The combined organic phases were then washed once with 150 l of water. After removal of the solvent from the organic phase by distillation under reduced pressure there remained 71.9 kg of an oil which comprised about 96.3% by weight of a mixture of 67.2 kg (278 mol) of 2-propanone O-[2-(4-chlorophenoxy)propyl]oxime (yield: 70%) and 2.1 kg (9 mol) of 2-propanone O-[2-(4-chlorophenoxy)-1-methylethyl]oxime and which solidified at 38° C. (ratio of isomers VIa/VIb=97:3).

c) Acidic cleavage of the O-phenoxyalkyloximes 71.9 kg of this mixture were mixed with 350 kg of 40% strength (1,430 mol) sulfuric acid. The reaction mixture was then heated to 80° C., and under 300 mbar 177 kg of acetone and water were removed by distillation over the course of 12 hours, continually replacing the water removed from the mixture in order to keep the concentration of acid in the reaction vessel constant. When the remaining solution was cooled to 20° C., 60.9 kg of precipitate separated out and comprised 99.5% by weight of the bisammonium sulfate of O-[2-(4-chlorophenoxy)propyl]hydroxylamine (content: 98.9% by weight; yield: 85%) and of O-[2-(4-chlorophenoxy)-1-methylethyl]hydroxylamine (0.6% by weight). This precipitate was washed successively with 175 kg each of water and toluene, and the crystals obtained in this way were dried at 40° C. under reduced pressure (isomer ratio=99.4:0.6).

bis-{O-[2-(4-Chlorophenoxy)propyl]hydroxylammonium} sulfate:

$^1$H-NMR (250.1 MHz; in d$^6$-dimethylsulfoxide): δ [ppm] =8.55 (3H, s); 7.33 (2H, d); 7.0 (2H, d); 4.7 (1H, m); 3.9 (2H, m); 1.22 (3H, d).

$^{13}$C-NMR (125.7 MHz; in d$^6$-dimethylsulfoxide): δ [ppm] =156.4 (tert. C) ; 129.4 (2CH); 124.5 (tert. C); 117.6 (2CH); 77.2 (CH$_2$); 71.6 (CH); 16.2 (CH$_3$).

d) Liberation of the O-phenoxyalkylhydroxylamines (I)

50 kg of 25% strength (312.5 mol) of sodium hydroxide solution were added to the crude product with stirring. The organic phase was separated off, the aqueous phase was extracted with 50 kg of toluene, and the toluene was removed from the combined organic phases by distillation. 48.3 kg of a mixture of the isomers O-[2-(4-chlorophenoxy)propyl]-hydroxylamine (Ia; 99.4% by weight; yield: 99%) and O-[2-(4-chlorophenoxy)-1-methylethyl]hydroxylamine (Ib: 0.6% by weight) remained.

The yield of O-[2-(4-chlorophenoxy)propyl]hydroxylamine was 59% based on 2-propanone O-(2-hydroxypropyl)oxime used.

Example 2

The starting material was, as in Example 1, a mixture of 2-propanone O-(2-hydroxypropyl)oxime and 2-propanone O-(2-hydroxy-1-methylethyl)oxime, but in the ratio 99.4:0.6, otherwise the procedure was as in Example 1. This resulted in O-[2-(4-chlorophenoxy)propyl]hydroxylamine (yield: 54%) and O-[2-(4-chlorophenoxy)-1-methylethyl] hydroxylamine in the ratio 99.98:0.02.

Example 3

The starting material was, as in Example 1, a mixture of 2-propanone O-(2-hydroxypropyl)oxime and 2-propanone O-(2-hydroxy-1-methylethyl)oxime, but in the ratio 76.2:23.8, otherwise the procedure was as in Example 1. This resulted in O-[2-(4-chlorophenoxy)propyl] hydroxylamine (yield: 56%) and O-[2-(4-chlorophenoxy)-1-methylethyl]hydroxylamine in the ratio 98.5:0.6.

Example 4

Preparation of O-(2-phenoxybutyl)hydroxylamine (VIa; R$^1$=ethyl; R$^2$, R$^3$=methyl; Ar=4-hydroxyphenyl)

The starting material was a mixture of 2-propanone O-(2-hydroxybutyl)oxime and 2-propanone O-(2-hydroxy-1-ethylethyl)oxime in the ratio 96.7:3.3. Phenol was used in place of 4-chlorophenol, otherwise the procedure was as in Example 1. This resulted in O-(2-phenoxybutyl) hydroxylamine (yield: 50%) and O-(2-phenoxy-1-ethylethyl)hydroxylamine in the ratio 99.8:0.2.

Example 5

Preparation of O-[2-(4-chlorophenoxy)propyl] hydroxylamine (VIa; R$^1$, R$^2$=methyl; R$^3$=ethyl; Ar=4-chlorophenyl)

The starting material was a mixture of 2-butanone O-(2-hydroxypropyl)oxime and 2-butanone O-(2-hydroxy-1-methylethyl)oxime in the ratio 92.7:7.3. The procedure was otherwise as in Example 1. This resulted in O-[2-(4-chlorophenoxy)propyl]hydroxylamine (yield: 25%) and O-[2-(4-chlorophenoxy)-1-methylethyl]hydroxylamine in the ratio 99.9:0.1.

Example 6

Preparation of 2-propanone O-[2-(4-chlorophenoxy)propyl] oxime and O-[2-(4-chlorophenoxy)propyl]hydroxylamine (Ia, VIa; R$^1$, R$^2$, R$^3$=methyl; Ar=4-chlorophenyl)

Variant 2 a) Preparation of the O-sulfonyloxyalkyloximes 4 kg (29 mol) of a mixture of 72.6% by weight 2-propanone O-(2-hydroxypropyl)oxime and 22.7% by weight 2-propanone O-(1-hydroxy-1-methylethyl)oxime (ratio of isomers IIa/IIb=76.2:23.8) were introduced into 4.6 kg (36 mol) of N,N-dimethylcyclohexylamine and 20 kg of o-xylene. A solution of 3.8 kg (33 mol) of methylsulfonyl chloride in 5 kg of o-xylene was added to this mixture at 5°–20° C., and the whole was then stirred at 25° C. for 1 hour.

b) Preparation of the O-phenoxyalkyloximes

After the crude product had been mixed with 7.5 kg of water, the organic phase was separated off and then heated with 15 kg of isopropanol, 3.9 kg (30 mol) of 4-chlorophenol and 8.4 kg of 40% strength (59 mol) potassium hydroxide solution at 80° C. for 10 hours. After this, most of the isopropanol and water was removed by distillation under reduced pressure, and two phases formed in the bottoms. The organic phase was separated off and distilled to remove substantially all of the o-xylene, to result in 4.92 kg of an oil which comprised 93.8% by weight of a mixture of 93.6% by weight (17.9 mol) 2-propanone O-[2-(4-chlorophenoxy) propyl]oxime (yield: 85%) and 6.4% by weight (1.2 mol) of 2-propanone O-[2-(4-chlorophenoxy)-1-methylethyl]oxime.

c1) Acidic cleavage of the O-phenoxyalkyloximes 160 g of a mixture comprising 96.9% by weight (0.64 mol) of 2-propanone O-[2-(4-chlorophenoxy)propyl]oxime and 3.1% by weight (0.02 mol) of 2-propanone O-[2-(4-chlorophenoxy)-1-methylethyl]oxime (ratio of isomers VIa/VIb=97:3) were mixed with 730 g of 21% strength (4.2 mol) hydrochloric acid. Distillation was carried out at 80° C. and 315 mbar with a reflux ratio of 12:1 to remove 202 g of a liquid which predominantly comprised water and acetone. Subsequently distillation was carried out at 68° C. and 180 mbar without reflux to remove 440 g of hydrochloric acid azeotropically. The residue (184 g) contained 70.6% by weight of the hydrochloride of O-[2-(4-chlorophenoxy) propyl]hydroxylamine (yield: 85%) in addition to 1.1% by weight of the hydrochloride of O-[2-(4-chlorophenoxy)-1-methylethyl]hydroxylamine (ratio of isomers Ia/Ib= 98.5:1.5).

O-[2-(4-Chlorophenoxy)propyl]hydroxylammonium chloride $^1$H-NMR (270.1 MHz; in d$^6$-dimethyl sulfoxide): δ [ppm] =11.25 (3H, s); 7.3 (2H, d); 7.05 (2H, d); 4.85 (1H, m); 4.25 (2H, m); 1.25 (3H, d).

$^{13}$C-NMR (125.7 MHz; in d$^6$-dimethyl sulfoxide): δ [ppm]=156.1 (tert. C); 129.4 (2 CH); 124.8 (tert. C); 117.7 (2 CH): 76.4 (CH$_2$); 71.3 (CH); 15.9 (CH$_3$).

c2) Reprecipitation with sulfuric acid

To this residue were added 120 g of water, 124 g of 25% strength (775 mmol) sodium hydroxide solution and 126 g of toluene; after mixing, the organic phase was separated off, and 76 g (2.38 mol) of methanol and 64 g of 50% strength (327 mmol) sulfuric acid were added, whereupon 132.8 g of bisammonium sulfates of O-[2-(4-chlorophenoxy)propyl] hydroxylamine (98.9% by weight) and O-[2-(4-chlorophenoxy)-1-methylethyl]hydroxylamine (1.1% by weight) precipitated. They were filtered off, washed with 190 g of toluene and then dried (82% yield based on the 2-propanone [2-(4-chlorophenoxy)propyl]oxime; isomer ratio 98.9:1.1).

d) Liberation of the O-phenoxyalkylhydroxylamines

The hydroxylamines were liberated as in Example 1. The yield of O-[2-(4-chlorophenoxy)propyl]hydroxylamine was 98%; the isomer ratio based on O-[2-(4-chlorophenoxy)-1-methylethyl]-hydroxylamine was 98.9:1.1.

We claim:

1. A process for preparing mixtures of isomers of O-phenoxyalkylhydroxylamines of the formulae Ia and Ib $$H_2N-O-CH_2-CH(R^1)-O-Ar \quad \text{(Ia)}$$

$$H_2N-O-CH(R^1)-CH_2-O-Ar \quad \text{(Ib)}$$

where $R^1$ is an alkyl group and Ar is the phenyl group which can carry non-aromatic substituents, and the corresponding salt mixtures, which comprises a) converting a mixture of isomers of O-(2-hydroxyethyl) oximes of the formulae IIa and IIb

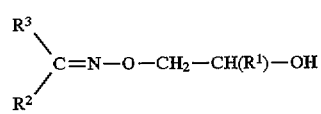
(IIa)

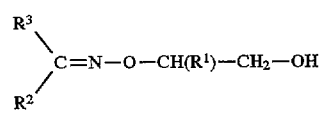
(IIb)

where $R^2$ is an alkyl group and $R^3$ is an alkyl or alkoxy group, or $R^2$ and $R^3$ form, together with the common carbon atom, a 5- to 7-membered isocyclic ring, with a sulfonyl halide of the formula III $$Hal-SO_2-R^4 \quad \text{(III)}$$

where $R^4$ is an organic radical, and Hal is halogen, in the presence of a base into the corresponding mixture of sulfonates IVa and IVb

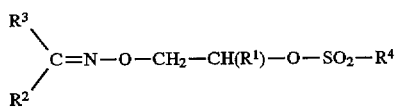
(IVa)

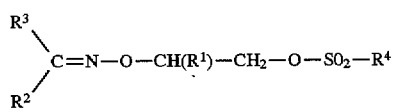
(IVb)

b) reacting this mixture of sulfonates in the presence of a base with a phenol of the formula V $$HO-Ar \quad \text{(V)}$$

to give a mixture of O-phenoxyalkyloximes of the general formulae VIa and VIb

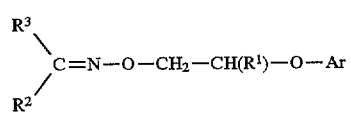
(VIa)

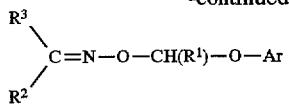
(VIa)

c) hydrolyzing this mixture in the presence of an acid and, optionally, d) liberating the O-phenoxyalkylhydroxylamines Ia and Ib from the resulting salts using a mineral base.

2. A process for preparing mixtures of O-phenoxyalkyloximes of the formulae VIa and VIb

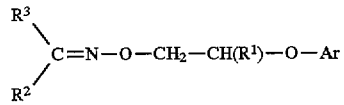
(VIa)

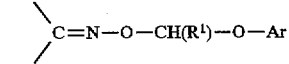
(VIa)

where $R^1$ to $R^3$ and Ar have the meanings given in claim 1, which comprises a) converting a mixture of isomers of O-(2-hydroxyethyl) oximes of the formulae IIa and IIb

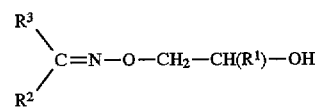
(IIa)

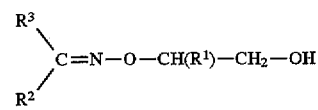
(IIb)

with a sulfonyl halide of the formula III $$Hal-SO_2-R^4 \quad \text{(III)}$$

where $R^4$ is an organic radical, and Hal is halogen, in the presence of a base into the corresponding mixture of sulfonates IVa and IVb

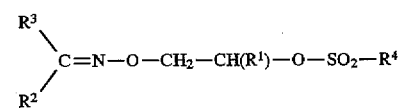
(IVa)

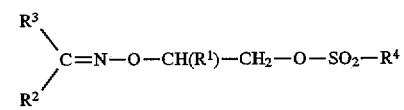
(IVb)

and b) reacting this mixture of sulfonates in the presence of a base with a phenol of the formula V $$HO-Ar \quad \text{(V).}$$

3. A process for preparing mixtures of isomers of O-phenoxyalkylhydroxylamines of the formulae Ia and Ib $$H_2N-O-CH_2-CH(R^1)-O-Ar \quad \text{(Ia)}$$

$$H_2N-O-CH(R^1)-CH_2-O-Ar \quad \text{(Ib)}$$

where $R^1$ and Ar have the meanings given in claim 1, and the corresponding salt mixtures, which comprises hydrolyzing a mixture of the O-phenoxyalkyloximes VIa and VIb

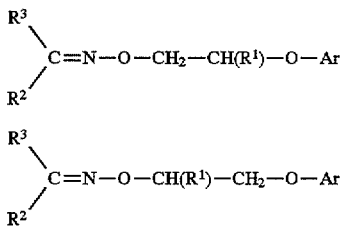

where $R^2$ is an alkyl group and $R^3$ is an alkyl or alkoxy group, or $R^2$ and $R^3$ form, together with the common carbon atom, a 5- to 7-membered isocyclic ring,
in the presence of an acid, and if desired reacting the salts of Ia and Ib produced thereby with a base.

4. A process as defined in claim 1, wherein an aliphatic tertiary amine is employed as base in process stage (a), and a mineral base is employed in process stage (b).

5. A process as defined in claim 1, wherein the mixture of sulfonates IVa and IVb is, without isolating it, reacted with the phenol V to give a mixture of O-phenoxyalkyloximes Ia and Ib.

6. A process as defined in claim 1, which starts from a mixture of IIa and IIb as produced in the reaction of a ketoxime VII

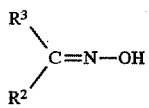

with an alkylene oxide VIII

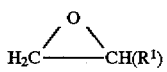

or the corresponding carbonate IX

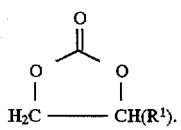

7. A process as defined in claim 1, wherein the hydrolysis of the mixture of VIa and VIb is carried out with hydrochloric acid, sulfuric acid or phosphoric acid.

8. A process as defined in any of claims 1, wherein and $R^3$ in the starting mixture are each methyl.

9. A process for preparing mixtures of isomers comprising the hydrochloride or sulfate salts of Ia and Ib as defined in claim 1, which comprises hydrolyzing a mixture of O-phenoxyalkyloximes VIa and VIb, where $R^2$ and $R^3$ are methyl, with aqueous hydrochloric acid or sulfuric acid, and continuously removing the acetone produced thereby from the reaction mixture.

10. A process as defined in claim 2, wherein an aliphatic tertiary amine is employed as base in process stage (a), and a mineral base is employed in process stage (b).

11. A process as defined in claim 2, wherein the mixture of sulfonates IVa and IVb is, without isolating it, reacted with the phenol V to give a mixture of O-phenoxyalkyloximes Ia and Ib.

12. A process as defined in claim 1 or 2, which starts from a mixture of IIa and IIb as produced in the reaction of a ketoxime VII

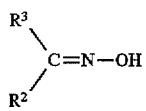

with an alkylene oxide VIII

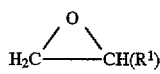

or the corresponding carbonate IX

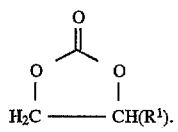

13. As process as defined in claim 3, wherein the hydrolysis of the mixture of VIa and VIb is carried out with hydrochloric acid, sulfuric acid or phosphoric acid.

14. A process as defined in claim 2, wherein $R^1$, $R^2$ and $R^3$ in the starting mixture are each methyl.

15. A process as defined in claim 3, wherein $R^1$, $R^2$ and $R^3$ in the starting mixture are each methyl.

16. A process for preparing mixtures of isomers comprising the hydrochloride or sulfate salts of Ia and Ib as defined in claim 3, which comprises hydrolyzing a mixture of O-phenoxylkyloximes VIa and VIb, where $R^2$ and $R^3$ are methyl, with aqueous hydrochloric acid or sulfuric acid, and continuously removing the acetone produced thereby from the reaction mixture.

17. A mixture of the isomers O-[2-(4-chlorophenoxy)propyl]-hydroxylammonium bisulfate

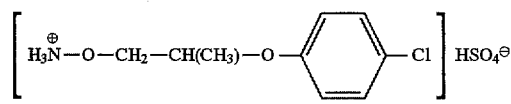

and O-[2-(4-chlorophenoxy)-1-methylethyl] hydroxylammonium bisulfate

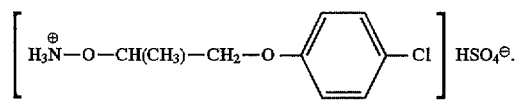

18. A mixture of the isomers O-[2-(4-chlorophenoxy)propyl]-hydroxylammonium chloride

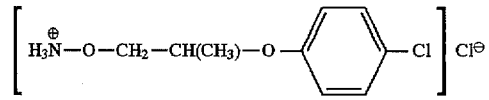

and O-[2-(4-chlorophenoxy)-1-methylethyl] hydroxylammonium chloride

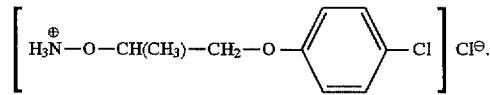

19. A mixture of the isomers 2-propanone O-[2-methylsulfonyloxypropyl]oxime

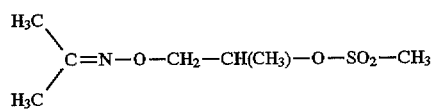
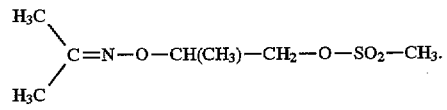
and 2-propanone O-[2-methyl sulfonyloxy-1-methylethyl] oxime
* * * * *

UNITED STATES PATENT AND TRADEMARK OFFICE
CERTIFICATE OF CORRECTION

PATENT NO.: 5,739,402

DATED: April 14, 1998

INVENTOR(S): RANG et al.

It is certified that error appears in the above-identified patent and that said Letters Patent is hereby corrected as shown below:

Col. 12, lines 5 and 20, "(VIa)" should be --(VIb)--; before "O-Ar" in the formula, insert --$CH_2$--.

Col. 13, claim 8, line 49, "any of claims" should be --claim--; after "wherein" insert --$R^1$, $R^2$--.

Signed and Sealed this

Twenty-fifth Day of August, 1998

Attest:

BRUCE LEHMAN

Attesting Officer

Commissioner of Patents and Trademarks